United States Patent
Vdovjak et al.

(10) Patent No.: US 10,762,984 B2
(45) Date of Patent: Sep. 1, 2020

(54) FEDERATED MASTER PATIENT INDEX FOR AUTONOMOUS HEALTHCARE ENTITIES

(71) Applicant: KONINKLIJKE PHILIPS N.V., Eindhoven (NL)

(72) Inventors: Richard Vdovjak, Eindhoven (NL); Anca Ioana Daniela Bucur, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 667 days.

(21) Appl. No.: 13/955,424

(22) Filed: Jul. 31, 2013

(65) Prior Publication Data

US 2014/0039929 A1 Feb. 6, 2014

Related U.S. Application Data

(60) Provisional application No. 61/678,379, filed on Aug. 1, 2012.

(51) Int. Cl.
*G16H 10/60* (2018.01)
*G06F 16/22* (2019.01)

(52) U.S. Cl.
CPC ......... *G16H 10/60* (2018.01); *G06F 16/2228* (2019.01)

(58) Field of Classification Search
CPC ...... G06F 17/30; G06F 17/321; G06F 19/322; G06F 16/2228; G06C 50/22; G06Q 10/10; G06Q 50/22; G16H 10/60
USPC ............................................................ 705/3
See application file for complete search history.

(56) References Cited

U.S. PATENT DOCUMENTS

| | | | | |
|---|---|---|---|---|
| 7,860,897 B2 * | 12/2010 | Dettinger et al. | ............ | 707/803 |
| 2005/0246205 A1 * | 11/2005 | Wang | ...................... | G06Q 50/24 705/3 |
| 2006/0287890 A1 * | 12/2006 | Stead | ...................... | G06Q 50/24 705/3 |
| 2011/0131062 A1 * | 6/2011 | Menschik | .............. | G16H 10/60 705/3 |

(Continued)

OTHER PUBLICATIONS

Integrated Healthcare Enterprise; IHE Technical Framework vol. 1, Integration Profiles. 2009. http://www.ihe.net/Technical_Framework/upload/IHE_ITI_TF_Vol1.pdf.

(Continued)

*Primary Examiner* — Hiep V Nguyen

(57) ABSTRACT

A method provides fully autonomous patient matching by entities of a federated healthcare system. The method includes receiving an electronically formatted query for a patient from an autonomous healthcare entity in a federation of healthcare entities. The query includes at least an identifier of the entity, a unique patient identifier of the patient generated by the entity, and demographics of the patient. The method further includes searching a federated master patient index stored in master patient index storage for an entry likely to correspond to the patient. The method further includes identifying an entry for the patient. The method further includes updating the identified entry to include at least the identifier of the entity, the unique patient identifier of the patient generated by the entity and the demographics.

17 Claims, 5 Drawing Sheets

(56) References Cited

U.S. PATENT DOCUMENTS

Figures 1, 2:
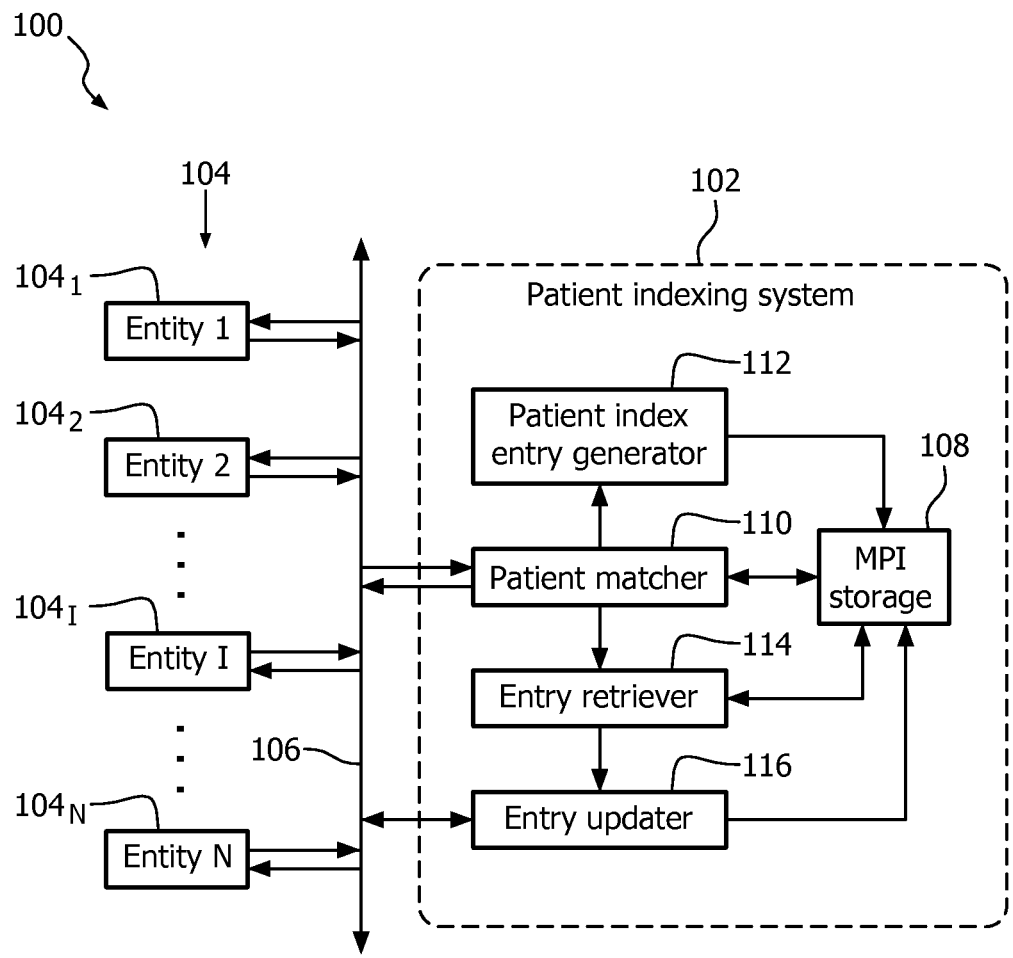

2013/0197940 A1* 8/2013 Garber ................ G06Q 50/24
705/3

OTHER PUBLICATIONS

Integrated Healthcare Enterprise; IHE Technical Framework vol. II, Transactions. 2010. http://www.ihe.net/Technical_Framework/index.cfm.

Integrated Healthcare Enterprise; IHE Technical Framework vol. III, Cross-Transaction Specification and Content Specifications. 2010. http://www.ihe.net/Technical_Framework/upload/IHE_ITI_TF_Vol3.pdf.

* cited by examiner

FEDERATED MASTER PATIENT INDEX FOR AUTONOMOUS HEALTHCARE ENTITIES

The following generally relates to a federated master patient index for autonomous healthcare entities.

It is more and more common that patients receive care from multiple healthcare providers geographically dispersed at multiple entities. As a consequence, the patient data for a patient, such as medical images and other relevant medical information, may be spread across multiple entities often stored in the local picture archiving and communication system (PACS) systems. In order to build a federated PACS, where the physical location of the data would become transparent to the clinical user, patient records that refer to a same patient in different healthcare entities need to be linked. In a federated PACS architecture, a patient registry is responsible for relating and linking the identifiers of the same (physical) patient in different entities based on demographic data.

Reconciling different patient identifiers that should be pointing to a single patient is commonly done by a Master Patient Index (MPI). Traditionally, an MPI is built as an authoritative source, i.e. it imposed a single truth over the result of the identifier matching process. This approach was conceived either within a single entity (with multiple sub-units) or with tightly coupled healthcare entities in mind, e.g. several geographically distributed clinics that conceptually belong under one hospital. The linkage is done either pair-wise or through a global patient identifier and in all cases it is assumed that the links are both transitive and symmetrical. If there is a single MPI authority and a single "global truth" for established links that match patients across the federated healthcare entities, symmetry and transitivity would have the following properties.

For symmetry, if a patient with Patient Identifier (PID)=123 at site A is linked by that site to a patient with PID=456 at site B, that link also becomes true for site B, which in practice may not be the case for autonomous hospitals, as site B would not want to be responsible for matching errors at a different site which may result in decisions endangering patients' health (if site A made an error and 123 and 456 do not actually identify the same patient, data from a different patient may be used in the clinical decision process). For transitivity, if site A subsequently also matches identifier 123 with another patient identifier at site C, PID=789, this automatically means that B:456 and C:789 are also linked, which in turn may again introduce error, exposing both site C and B to consequences by a potentially erroneous match done at site A.

While in the ideal world without matching mistakes, symmetry and transitivity are desired properties, in the real world of a loosely coupled federation, an entity cannot control the consistency of its own data. For this reason, current centralized solutions cannot be used in federations composed of autonomous healthcare entities that want to share their data while still remaining in control for their data consistency and maintaining their autonomy. In other words, the single authoritative truth assumption is not applicable in an autonomous federation e.g. in a loosely coupled regional healthcare entities. Within such a loosely coupled autonomous federation, a participating organization is responsible to establish its own links among the patient identifiers that point to the same person, and there is no federation-wide authority which establishes a "global truth".

In view of the foregoing, there if an unresolved need for other approaches for federations composed of autonomous healthcare entities.

Aspects described herein address the above-referenced problems and others.

In one aspect, a method provides fully autonomous patient matching by federated healthcare entities. The method includes receiving an electronically formatted query for a patient from an autonomous healthcare entity in a federation of healthcare entities. The query includes at least an identifier of the, a unique patient identifier of the patient generated by the entity, and demographics of the patient. The method further includes searching a federated master patient index stored in master patient index storage for an entry likely to correspond to the patient. The method further includes identifying an entry for the patient. The method further includes updating the identified entry to include at least the identifier of the entity, the unique patient identifier of the patient generated by the entity and the demographics.

In another aspect, a system provides fully autonomous patient matching by federated healthcare entities. The system includes a patient matcher that receives an electronically formatted query for a patient from an autonomous healthcare entity in a federation of healthcare entities. The query includes at least an identifier of the entity and a unique patient identifier of the patient generated by the entity. The patient matcher searches a federated master patient index stored in master patient index storage for an entry for the patient. The system further includes an entry retriever that retrieves an entry for the patient in response to the patient matcher identifying the entry as likely to corresponding to a same patient. The system further includes an entry updater that updates the retrieved entry to include at least the identifier of the entity and the unique patient identifier of the patient generated by the entity.

In another aspect, a computer readable storage medium is encoded with computer readable instructions, which, when executed by a processer, causes the processor to: receive an electronically formatted query for a patient from an autonomous healthcare entity in a federation of healthcare entities, wherein the query includes at least an identifier of the entity and a unique patient identifier of the patient generated by the entity, search a federated master patient index stored in master patient index storage for an entry for the patient, wherein the master patient index includes, for each patient registered in an entity in the federation of healthcare entities, an entry with all of the unique patient identifiers identified as likely to refer to a same patient and links established by each entity where that patient is potentially known, identify an entry for the patient, and update the identified entry to include at least the identifier of the entity and the unique patient identifier of the patient generated by the entity.

The invention may take form in various components and arrangements of components, and in various steps and arrangements of steps. The drawings are only for purposes of illustrating the preferred embodiments and are not to be construed as limiting the invention.

FIG. 1 schematically illustrates an example system including a federated patient indexing system for autonomous healthcare entities.

FIG. 2 illustrates an example master patient index of the federated patient indexing system of FIG. 1.

Figure 3:
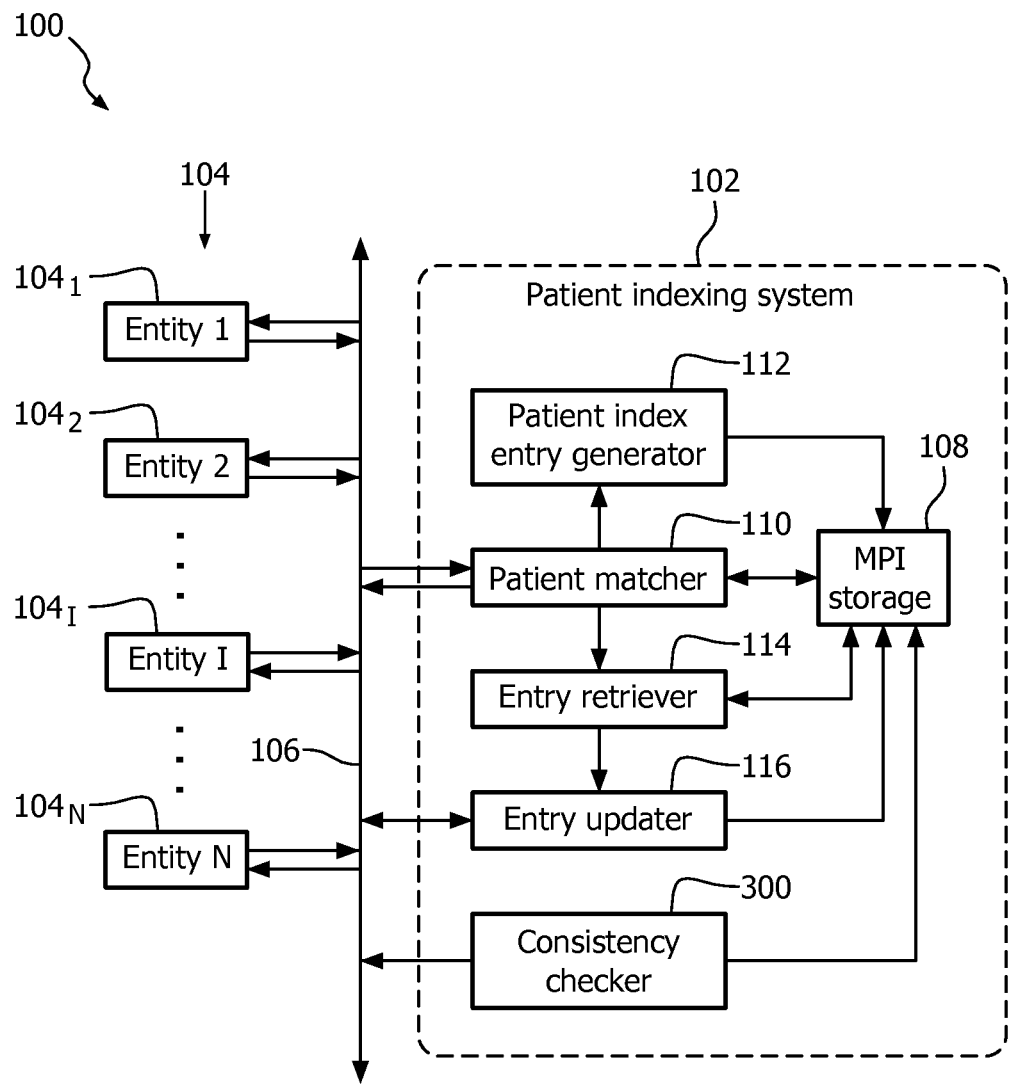

FIG. 3 schematically illustrates the example federated patient indexing system of FIG. 1 with an optional consistency checker.

Figure 4:
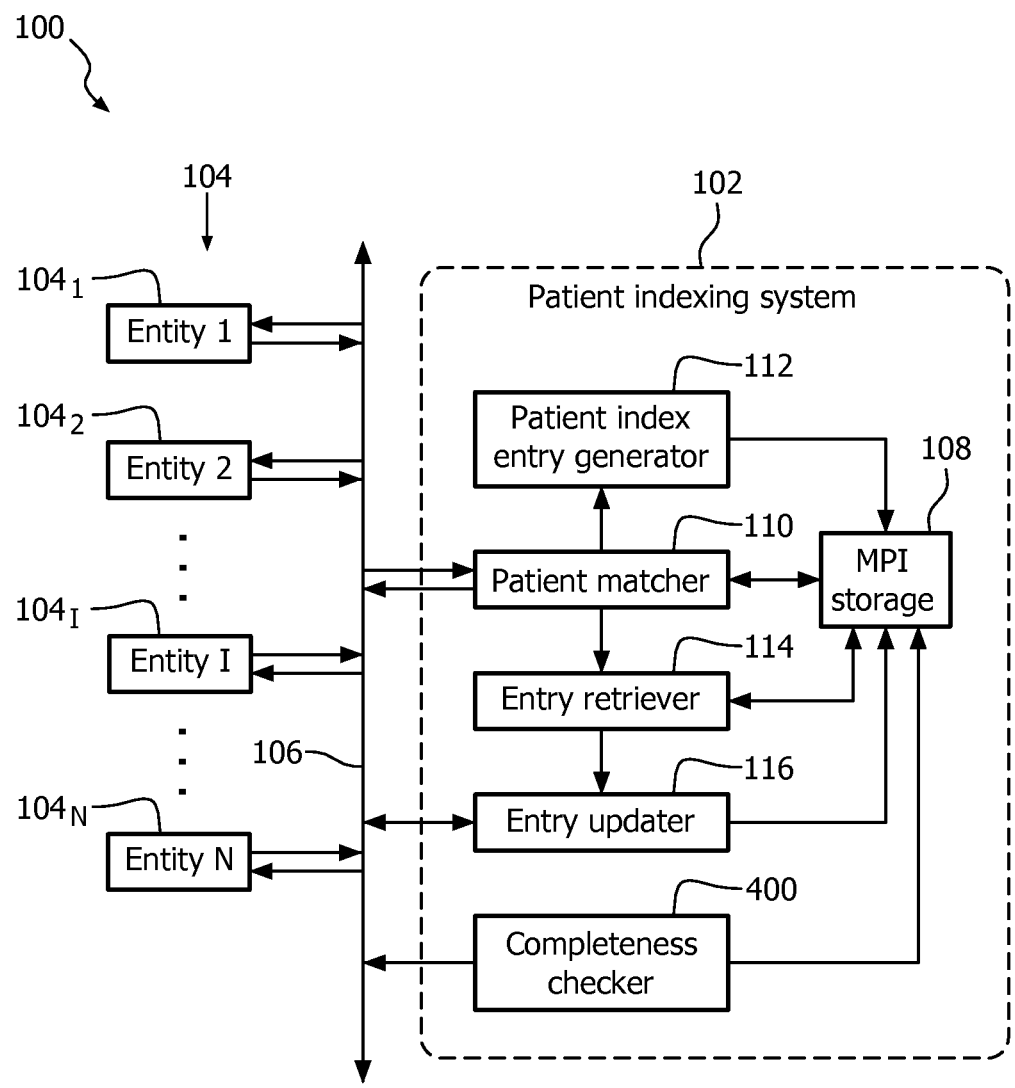

FIG. 4 schematically illustrates the example federated patient indexing system of FIG. 1 with an optional completeness checker.

Figure 5:
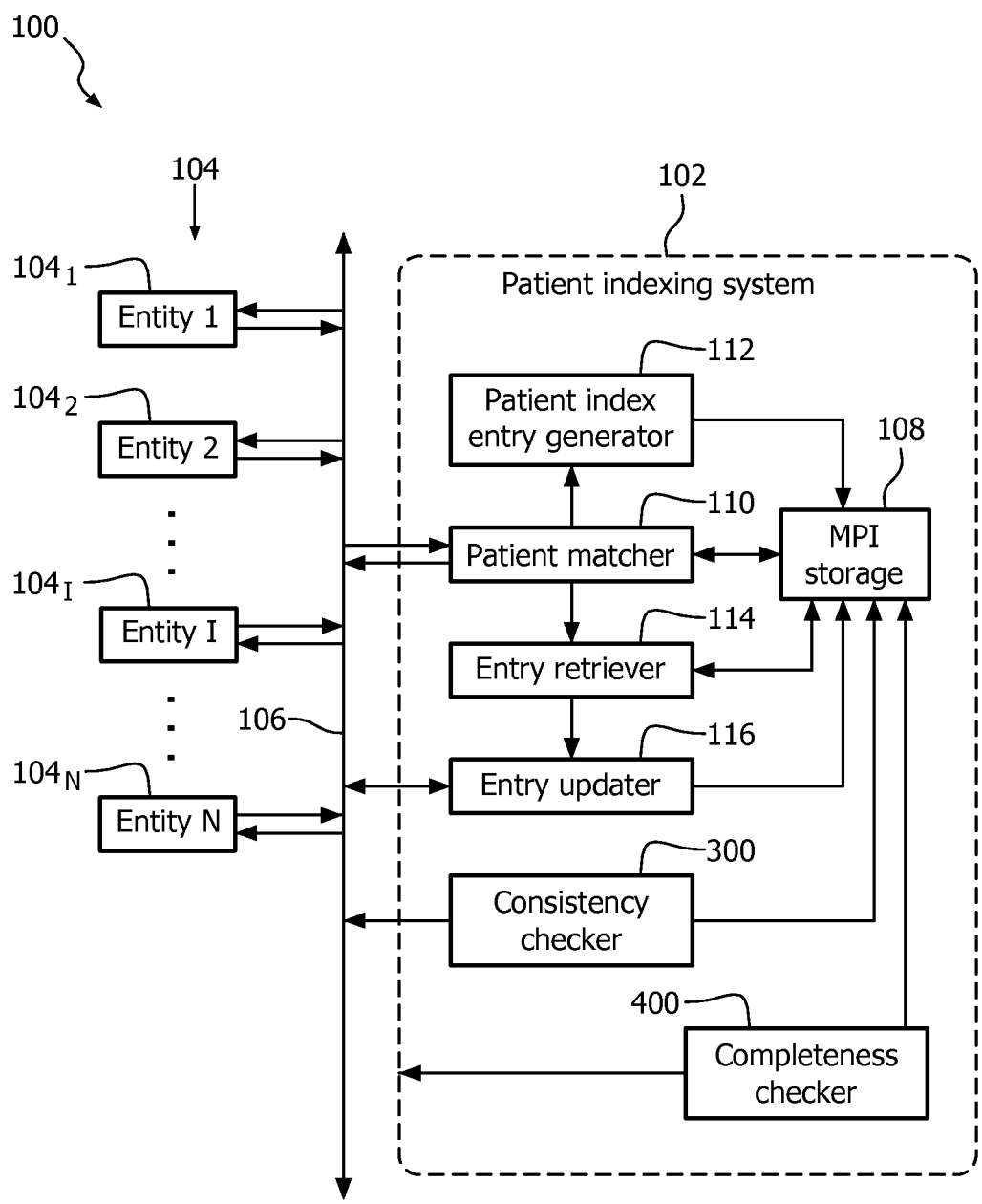

FIG. 5 schematically illustrates the example federated patient indexing system of FIG. 1 with both, the optional consistency checker and the optional completeness checker.

Figure 6:
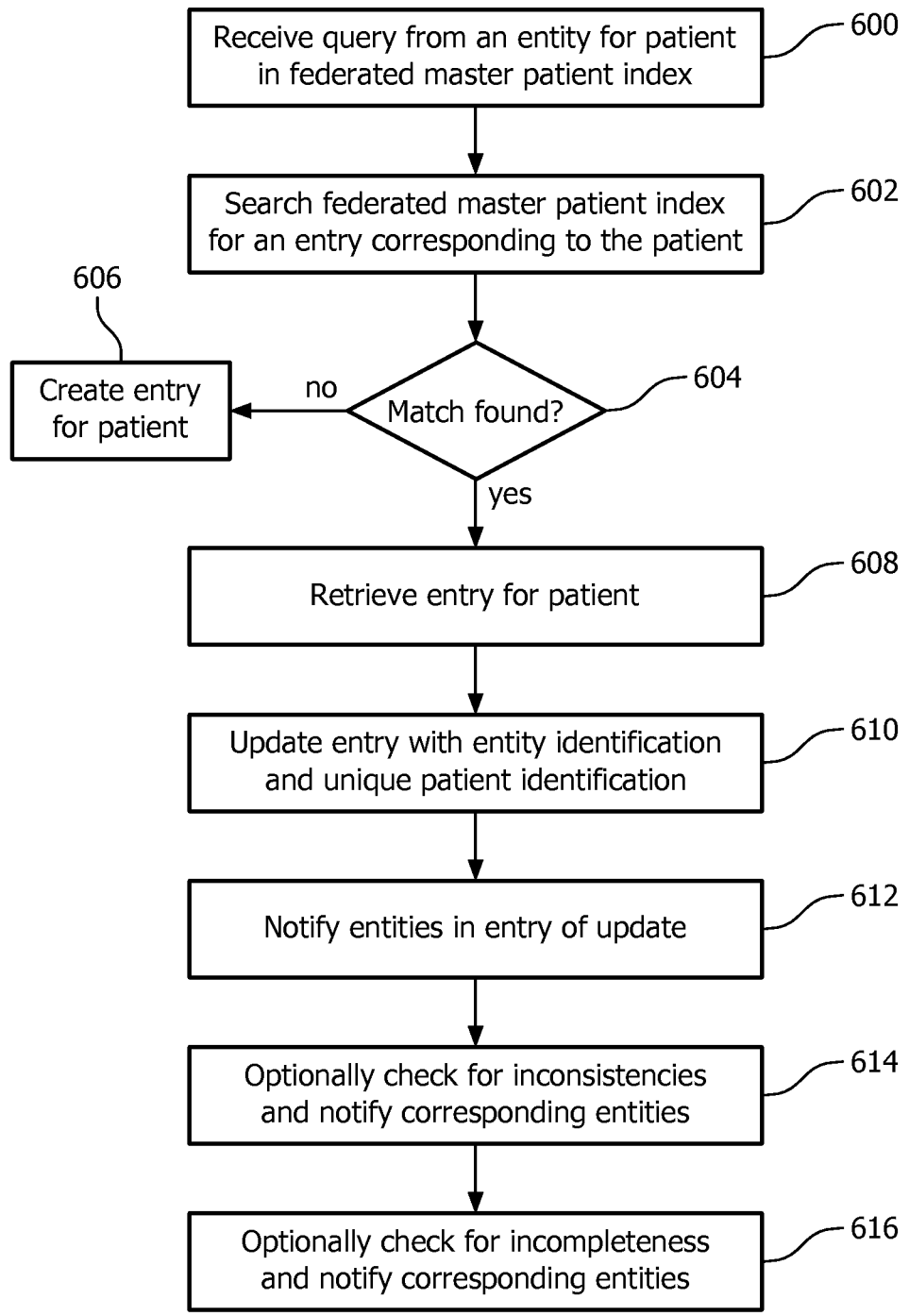

FIG. 6 illustrates a method for implementing a federated patient indexing system for autonomous healthcare entities.

The following describes a federation of healthcare entities with fully autonomous patient matching at every node of the federation. For this approach, a federated master patient indexing system allows for individual patient matching by participating entities. Results of the matching are stored in a data structure that contains for each patient registered in at least one institution in the federation all local identifiers and the available demographic data that may refer to the same patient and the links established by each institution where that patient is potentially known, allowing for non-transitive and non-symmetrical matching links.

Initially referring to FIG. 1, a system 100 includes a patient indexing system 102 and one or more healthcare entities $104_1, \ldots, 104_N$, where N is an integer equal to or greater than one. Collectively, the one or more healthcare entities $104_1, \ldots, 104_N$ are referred to herein as healthcare entities 104. Examples of the healthcare entities 104 include, but are not limited to, hospitals, clinics, urgent cares, doctors' offices, imaging centers, one or more groupings thereof, and/or other entity that produces and/or utilizes electronically formatted patient information in connection with a patient thereof.

The healthcare entities 104 are autonomous in that each healthcare entity 104 generates and maintains its own unique patient identifiers for its patients. For example, a first time a patient A registers with the healthcare entity $104_1$, the healthcare entity $104_1$ generates a unique patient identifier for the patient A, and this unique patient identifier is used to identify the patient A throughout the healthcare entity $104_1$ each time the patient A registers with the healthcare entity $104_1$. However, the healthcare entity $104_2$ generates a different unique patient identifier for the patient A when the patient A registers with the healthcare entity $104_2$ the first time.

The healthcare entities 104 and the patient indexing system 102 communicate, in the illustrated embodiment, through a network 106.

The patient indexing system 102 includes master patient index (MPI) storage 108, which comprises physical, non-transitory computer readable storage medium. A master patient index for all the patients of all the healthcare entities 104 is stored thereon. Generally, the master patient index is a data structure that contains for each patient registered in at least one healthcare entity 104 in the federation all local identifiers and, optionally, available demographic data that may refer to the same patient and the links established by each healthcare entity 104 where that patient is potentially known, allowing for non-transitive and non-symmetrical matching links.

The patient indexing system 102 includes a patient matcher 110 that, in response to a patient query from a healthcare entity 104, searches the MPI storage 108 for an entry corresponding to the patient. Generally, the query includes the entity identifier, the unique patient identifier generated by the entity, and demographic data. Where the query is for a list of entities 104 and patient identifiers likely corresponding to a patient, the patient matcher 110 retrieves this information from the MPI storage 108, if this information exists, and returns it to the querying entity 104, which can then communicate with another entity 104 about the patient using the appropriate unique patient identifier.

The patient indexing system 102 further includes a patient index entry generator 112 that, in response to the search failing to find an entry likely corresponding to the patient, generates an entry for the patient. The newly generated entry includes at least the unique identifier of the entity 104, the unique identifier of the patient, and the patient demographics. The patient index entry generator 112 stores the newly generated entry in the master patient index of the MPI storage 108.

The patient indexing system 102 also includes a patient entry retriever 114 that, in response to the search successfully finding an entry likely corresponding to the patient, retrieves the corresponding entry in the master patient index of the MPI storage 108. The entry generally includes at least indicia indicating the other entities 104 at which the patient has registered, the unique patient identifiers and the demographics. As discussed in greater detail below, this information may also indicate whether each of the other entities 104 in the entry have confirmed, rejected or not evaluated the links in the entry to patient identifiers of the other entities 104.

The patient indexing system 102 further includes an entry updater 116 that updates the retrieved entry. This includes adding at least a unique identifier of the entity 104, the unique identifier of the patient and the demographics, and linking this information to the retrieved entry. The entry updater 116, for each of the other entities 104 in the entry, also adds indicia indicating that this link has not been confirmed nor rejected by the other entities 104. The entry updater 116 notifies all the entities 104 in the entry that the entry has been updated and the links therein can be evaluated.

Where a notified entity 104 evaluates the new entry, confirms the new entry is likely or certain to correspond to the corresponding patient and conveys a signal indicative of the confirmation to the patient indexing system 102, the entry updater 116 updates the entry to include indicia indicating the confirmation. Where the notified entity 104 evaluates the new entry, rejects the new entry as being likely or certain to correspond to the corresponding patient and conveys a signal indicative of the rejection to the patient indexing system 102, the entry updater 116 updates the entry to include indicia indicating the rejection.

It is to be appreciated that the patient indexing system 102 can be implemented via one or more microprocessor executing computer readable and executable instructions stored on computer readable storage medium such as physical memory and/or other non-transitory medium. Additional or alternatively, the one or more microprocessor can execute readable and executable instructions carried by a carrier wave, signal and/or other transitory medium.

FIG. 2 illustrates an example entry 200 of the master patient index. In this example, the data structure is a matrix with row and column headers indicating the entities and the unique patient identifiers that were identified by the patient matcher 110 as likely to correspond to the same patient. However, other data structures such as an indexed list, which may facilitate minimizing memory and/or disk usage, and/or other data structure are also contemplated herein.

When an entity/unique patient identifier is first added to the entry 200, the cell corresponding to the entity/unique patient identifier matched with the entity/unique patient identifier (i.e., a cell along the diagonal, or a cell M[I,J], where I=J) is populated with a value of "1." For example, the cells for A:123/A:123 (M[1,1]), B:456/B:456 (M[2,2]), C:789/C:789 (M[3,3]) and D:101/D:101 (M[4,4]) are each populated with a value of "1." However, a cell corresponding to the entity/unique patient identifier matched with another entity/unique patient identifier is populated with a value of "0." For example, the cells for A:123/D:101 (M[1, 4]) and D:101/A:123 (M[4,1]) are each populated with a value of "0."

When an entity 104 for a given row confirms a match between the unique patient identifier and a unique patient identifier of another entity 104, the entry updater 116 updates the corresponding cell with a value of "1." For example, the cell for A:123/B:456 (M[1,2]) is populated with a value of "1," which indicates the entity A has confirmed patient 456 of entity B corresponds to the same patient. When the entity 104 for a given row rejects a match between the unique patient identifier and the unique patient identifier of another entity 104, the entry updater 116 updates the corresponding cell with a value of "−1." For example, the cell for B:456/A:123 (M[2,1]) is populated with a value of "−1," which indicates the entity B has rejected the match indicating the patient 123 of entity A corresponds to the same patient.

When an entity 104 queries the patient indexing system 100 for a patient, in one instance, the entity 104 receives the entry 200, which includes the linked patients of the different entities 104 along with the indicia indicating whether a match has been confirmed, rejected or not evaluated. The receiving entity 104 determines how to handle instances in which cells include "0" or "−1." If another entity 104 (entity E) identifies a newly registered patient "000" and this patient is found to correspond with the patient for the entry 200, another row and column would be added with header "E:000."

An alternative implementation, the data structure could store, for each local patient identifier, an entry in the master patient index containing an array of local identifiers to which a current local identifier is linked. In this case, each local identifier owns a single entry, but appears in all entries belonging to identifiers that link to it.

Variations are discussed next.

FIG. 3 illustrates a variation in which the patient indexing system 100 further includes a consistency checker 300. The consistency checker 300 checks each entry stored in the MPI storage 108 and identifies cell pairs with direct contradiction, such as cells symmetric about the diagonal having values of "−1" and "1" (e.g., cells M[2,1] and M[1,2] in FIG. 2, both corresponding to the pair A:123/B:456). Indirect contradictions can be found by computing the transitive closure for all matched identifiers and then searching for direct inconsistencies. The consistency checker 300 then notifies the corresponding entities 104 about the inconsistency. The entities 104 may or may not re-evaluate the match, preserving their local autonomy.

FIG. 4 illustrates a variation in which the patient indexing system 100 further includes a completeness checker 400. The completeness checker 400 checks each entry stored in the MPI storage 108 and identifies cells with a value of "0" (e.g., cell M[3,1], or C:789/A:123. In one instance, completeness suggestions are found by computing the transitive closure for all matched identifiers and whenever there was a cell in the matrix with "0" which was changed by the transitive closure to "1" or "−1" the corresponding suggestion is conveyed to the corresponding entity 104. The completeness checker 400 then notifies the corresponding entity 104 that the match has neither been confirmed nor rejected. The entity 104 may or may not evaluate the match, preserving their local autonomy.

In another variation, the patient indexing entry includes both the consistency checker 300 and the completeness checker 400 as shown in FIG. 5.

FIG. 6 illustrates an example method for implementing a federated patient indexing system for autonomous healthcare entities. It is to be appreciated that the ordering of the acts in the methods described herein is not limiting. As such, other orderings are contemplated herein. In addition, one or more acts may be omitted and/or one or more additional acts may be included.

At 600, an autonomous entity queries a federated patient indexing system for an entry in a master patient index for a patient newly registered at the entity.

At 602, the federated patient indexing system searches the master patient index for an entry corresponding to the patient.

If at 604 the patient is not found in the master patient index, then at 606 an entry is generated for the patient in the master patient index, and the entry is populated at least with an entity identifier and a unique patient identifier created for the patient by the entity.

However, if at 604 a potential patient match is identified in the master patient index, then at 608 the corresponding entry for the patient is retrieved.

At 610, the entry is updated to include at least the entity identifier and the unique patient identifier created for the patient by the entity.

At 612, the entities in the entry are notified of the change. One or more of the notified entries independently decide whether to evaluate and confirm or reject the match.

At 614, optionally, the master patient index is checked for inconsistencies in which one entity rejects a match whereas another entity confirms the match, and the entities are notified of the inconsistency. One or both of the notified entries independently decide how to handle the inconsistency.

At 616, optionally, the master patient index is checked for completeness in which an entity in an entry has not evaluated a match (i.e., neither confirms nor rejects a match), and the entity is notified of the incompleteness. The notified entries independently decide how to handle the incompleteness.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The foregoing is well-suited for a federated PACS (picture archiving and communication system) system, a federated EMR (electronic medical record) system, and/or other federated system that can support patient data sharing in an autonomous federation of healthcare entities. Such a system allows for mitigating "undesired" properties of symmetry and transitivity by. The links maintained in the mast patient index are unidirectional, and no unique global identifiers are assigned to groups of linked local identifiers.

Furthermore, the foregoing may also become an extension to the existing Integrated Healthcare Enterprise (IHE) profiles such as Patient Identity Cross Referencing (PIX), which at the moment, only assumes a single authoritative source of linkage and hence it is unsuitable for truly autonomous federations.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method that provides fully autonomous patient matching by federated healthcare entities, comprising:
   receiving, by a processor of a patient indexing system, an electronically formatted query for a patient from a processor of an autonomous healthcare entity in a federation of healthcare entities, wherein the query includes at least an identifier of the entity, a unique patient identifier of the patient generated by the entity, and demographics of the patient, wherein each autonomous healthcare entity generates and maintains its own unique patient identifiers for its patients, and wherein the patient indexing system is an entity separate from the autonomous healthcare entities in the federation of healthcare entities;
   searching, with the processor of the patient indexing system, a federated master patient index stored in master patient index storage of the patient indexing system for an entry likely to correspond to the patient, wherein the federated master patient index includes, for patients registered in autonomous healthcare entities in the federation of healthcare entities, entries with all of the unique patient identifiers identified as likely to refer to a same patient and links established by each entity where that patient is potentially known;
   linking, with the processor of the patient indexing system, the entry likely to correspond to the patient in the federated master patient index for the patient to the unique patient identifier, thereby creating a link, wherein the link is non-transitive; and
   updating, with the processor of the patient indexing system, the linked entry in the federated master patient index to include at least the identifier of the entity, the unique patient identifier of the patient generated by the entity and the demographics, wherein, prior to the updating, the federated master patient index did not include the identifier of the entity, the unique patient identifier of the patient generated by the entity and the demographics.

2. The method of claim 1, further comprising:
   notifying each entity in the entry that the entry has been updated to include another unique patient identifier likely to refer to a patient corresponding to the entry.

3. The method of claim 1, further comprising:
   updating the entry with indicia indicating the added unique patient identifier has not been confirmed or rejected by each of the notified entities.

4. The method of claim 3, further comprising:
   receiving, from a notified entity, a signal indicating the notified entity confirmed the added unique patient identifier corresponds to the patient.

5. The method of claim 4, further comprising:
   updating the entry with indicia indicating the notified entry confirmed the added unique patient identifier corresponds to the patient.

6. The method of claim 4, further comprising:
   searching the master patient index for inconsistencies between entities regarding whether the added unique patient identifier corresponds to the patient.

7. The method of claim 6, further comprising:
   notifying entities of an inconsistency in response to identifying an inconsistency in the master patient index.

8. The method of claim 3, further comprising:
   receiving, from a notified entry, a signal indicating the notified entry rejected the added unique patient identifier as corresponding to the patient.

9. The method of claim 8, further comprising:
   updating the entry with indicia indicating the notified entry rejected the added unique patient identifier as corresponding to the patient.

10. The method of claim 3, further comprising:
    searching the master patient index for the indicia indicating the added unique patient identifier has not been confirmed or rejected by a notified entity.

11. The method of claim 10, further comprising:
    notifying the entity that the added unique patient identifiers has not been confirmed or rejected by a notified entity.

12. A system that provides fully autonomous patient matching by federated healthcare entities, comprising:
    a federation of autonomous healthcare entities, wherein at least one of the entities generates an electronically formatted query for a patient from the at least one of the entities, wherein the query includes at least an identifier of the entity, a unique patient identifier of the patient generated by the entity, and demographics of the patient, wherein each autonomous healthcare entity generates and maintains its own unique patient identifiers for its patients;
    a patient indexing system, which is separate from the autonomous healthcare entity, including:
      a federated master patient index stored in master patient index storage;
      a patient matcher that receives the electronically formatted query and searches the federated master patient index stored in the master patient index storage for an entry likely to correspond to the patient, wherein the federated master patient index includes, for patients registered in autonomous healthcare entities in the federation of healthcare entities, entries with all of the unique patient identifiers identified as likely to refer to a same patient and links established by each entity where that patient is potentially known and links the entry, which is likely to correspond to the patient to the unique patient identifier, wherein the link is non-transitive;
      an entry retriever that retrieves the entry likely to correspond to the patient for the patient in response to the patient matcher linking the entry; and
      an entry updater that updates the retrieved entry to include at least the identifier of the entity and the unique patient identifier of the patient generated by the entity, wherein, prior to the updating, the federated master patient index did not include the identifier of the entity, the unique patient identifier of the patient generated by the entity and the demographics.

13. The system of claim 12, wherein the entry updater updates the entry with indicia indicating the added unique patient identifiers has not been confirmed or rejected by each of the notified entities and notifies each entity in the entry that the entry has been updated to include another unique patient identifier likely to refer to a patient corresponding to the entry.

14. The system of claim 13, wherein the entry updater receives a signal from a notified entity indicating the notified entity confirmed or rejected the added unique patient identifier as corresponding to the patient and updates the entry with indicia indicating whether the entity confirmed or rejected the added unique patient identifier.

15. The system of claim 12, further comprising:
a consistency checker that searches the master patient index for inconsistencies between entities regarding whether the added unique patient identifiers corresponds to the patient and that notifies entities of an inconsistency in response to identifying an inconsistency in the master patient index.

16. The system of claim 12, further comprising:
a completeness checker that searches the master patient index for the indicia indicating the added unique patient identifiers has not been confirmed or rejected by a notified entity and that the entity that the added unique patient identifiers has not been confirmed or rejected by a notified entity.

17. The system of claim 12, wherein the entry includes a matrix, wherein a cell includes an indicator that indicates whether an entity confirmed or rejected a unique patient identifier generated by another entity or has not evaluated the unique patient identifier.

\* \* \* \* \*